US00PP30062P2

(12) United States Plant Patent
Finn

(10) Patent No.: US PP30,062 P2
(45) Date of Patent: Jan. 8, 2019

(54) BLACKBERRY PLANT NAMED 'GALAXY'

(50) Latin Name: ***Rubus* subg. *Rubus* Watson.**
Varietal Denomination: Galaxy

(71) Applicant: The United States of America, as Represented by the Secretary of Agriculture, Washington, DC (US)

(72) Inventor: Chad E. Finn, Corvallis, OR (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/731,505

(22) Filed: Jun. 20, 2017

(51) Int. Cl.
*A01H 5/08* (2018.01)

(52) U.S. Cl.
USPC ..... Plt./203

(58) Field of Classification Search
USPC ..... Plt./203
See application file for complete search history.

*Primary Examiner* — Susan McCormick Ewoldt
(74) *Attorney, Agent, or Firm* — John Fado; Gail Poulos

(57) ABSTRACT

A new and distinct blackberry cultivar that originated from seed produced from a cross between the female blackberry plant 'ORUS 1393-1' (unpatented) and the male blackberry plant 'Triple Crown' (unpatented). This new blackberry is unique in that it contains all three commercial blackberry types (trailing, erect, and semi-erect) in its pedigree as either a parent or a grandparent. This new blackberry cultivar can be distinguished by being early ripening for a semi-erect blackberry, by its medium-large sized, firm berries with tough skin and very good flavor, by its medium to high yields borne on a vigorous plant with a semi-erect type growth habit and by its completely thornless canes.

4 Drawing Sheets

Latin name of the genus and species of the plant claimed: 'Galaxy' is a blackberry plant that is *Rubus* subg. *Rubus* Watson.

Variety denomination: The new blackberry plant claimed is of the variety denominated 'Galaxy' *Rubus* subg. *Rubus* Watson.

BACKGROUND OF THE INVENTION

The present invention relates to a new and distinct blackberry cultivar designated 'Galaxy' and botanically known as *Rubus* subg. *Rubus* Watson. This new blackberry cultivar was discovered in Corvallis, Oreg. in August 2003 and originated from a cross between the female blackberry plant 'ORUS 1393-1' (unpatented) and the thornless, male parent blackberry plant 'Triple Crown' (unpatented). 'Galaxy' shares the same parents as 'Eclipse' (U.S. Plant patent application Ser. No. 15/731,503) but it was selected one year earlier from a different cross of the same parents. 'ORUS 1393-1' (unpatented) was a selection from a cross of the thornless erect blackberry 'Navaho' (U.S. Plant Pat. No. 6,679) and a thorny trailing blackberry selection ORUS 1122-1 (unpatented). Therefore, 'Galaxy' represents a unique pedigree with all three of the main types of blackberry used in breeding for commercial cultivars represented in its pedigree as it's paternal parent is a hybrid of an erect and trailing blackberry genotype and its maternal parent is a semi-erect blackberry. 'Galaxy's' spinelessness was originally derived from 'Merton Thornless' (U.S. Plant Pat. No. 571). The original seedling of the new cultivar was asexually propagated at a nursery in Benton County, Oreg. The new cultivar was established in vitro from a cane cutting and microcuttings have been taken and rooted from this sort of culture. The present invention has been found to be stable and reproduce true to type through successive asexual propagations.

SUMMARY OF THE INVENTION

The following are the most outstanding and distinguishing characteristics of this new cultivar when grown under normal horticultural practices in Oregon. 1. High plant vigor as compared to semi-erect blackberry 'Loch Ness' (U.S. Plant Pat. No. 6,782); 2. Semi-erect growth habit with thornless canes; 3. Early date for 50% of ripe fruit compared to 'Chester Thornless' (unpatented) and 'Triple Crown' (unpatented) 4. Firm fruit with tough skin compared to 'Triple Crown' (unpatented); 5. Excellent flavor compared to 'Chester Thornless' (unpatented) and 'Loch Ness' (U.S. Plant Pat. No. 6,782); 6. Larger, less symmetrically shaped fruit than those for its sibling 'Eclipse' (plant patent applied for), that also ripens earlier.

BRIEF DESCRIPTION OF THE PHOTOGRAPHS

This new blackberry plant is illustrated by the accompanying photographs that show the flowers, fruit and entire plants; the colors shown are as true as can be reasonably obtained by conventional photographic procedures.

Figure 1:
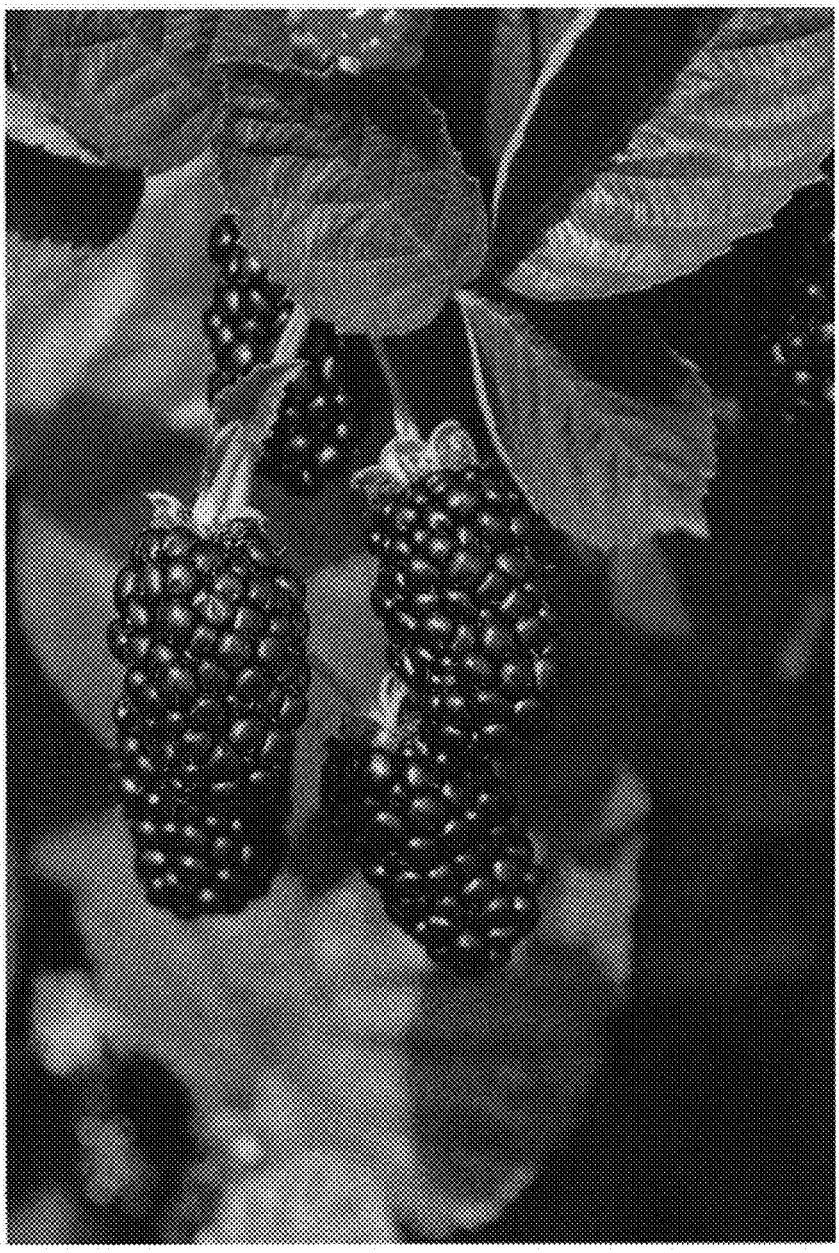

FIG. 1. shows typical fruiting cluster with ripe fruit 'Galaxy'.

Figure 2:
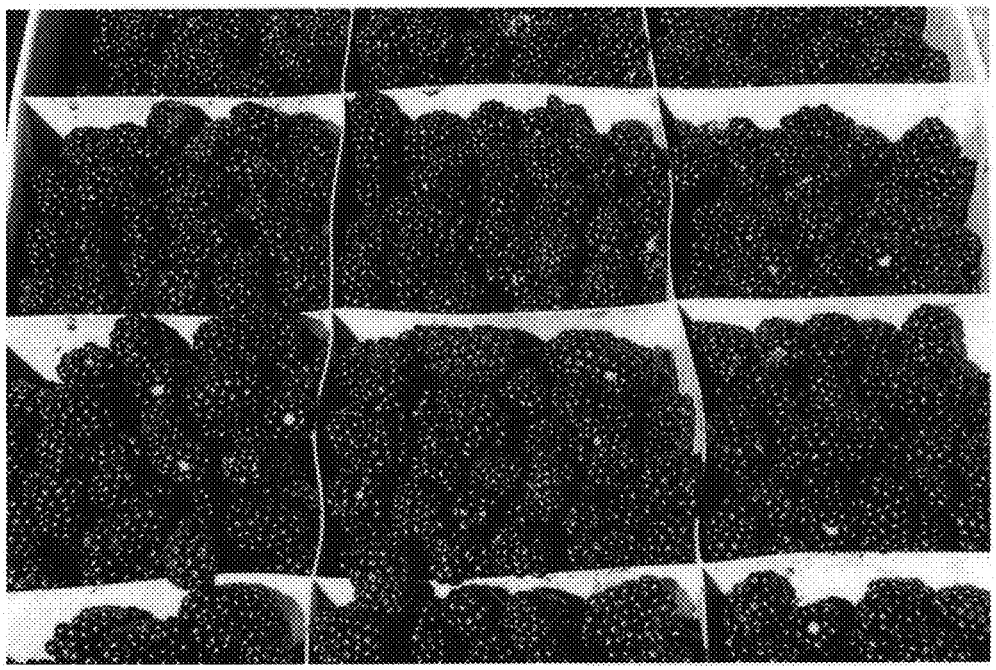

FIG. 2. shows an entire flat of harvested 'Galaxy' fruit.

Figure 3:
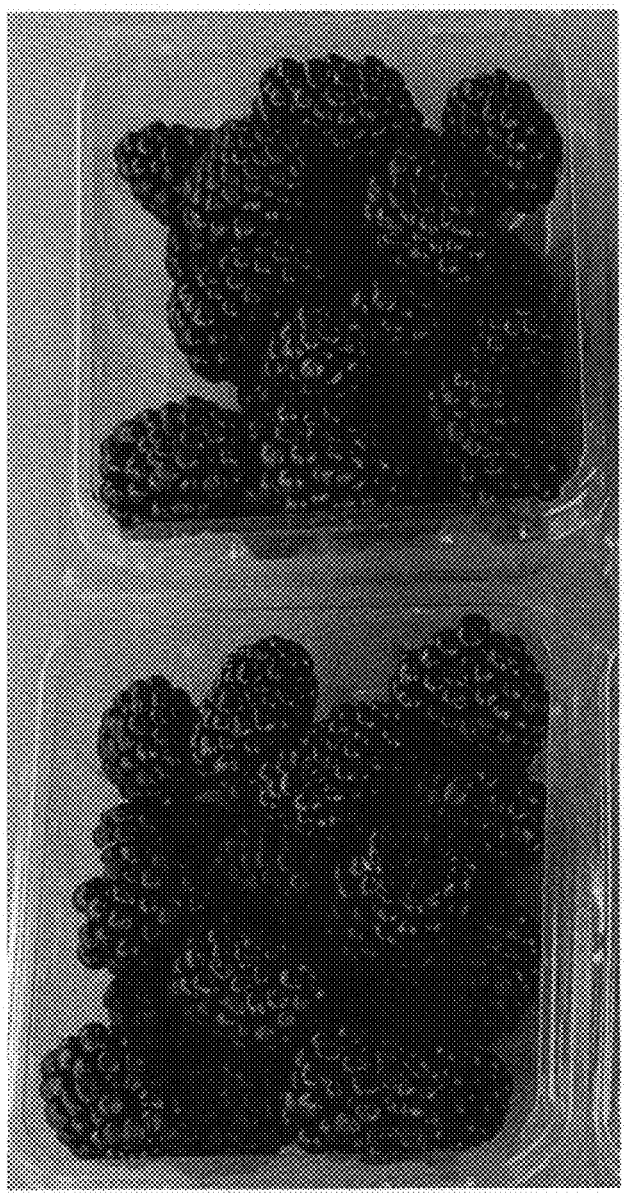

FIG. 3. shows two clamshells of 'Galaxy' fruit after 14 days of refrigerated storage at ~1° C.

Figure 4:
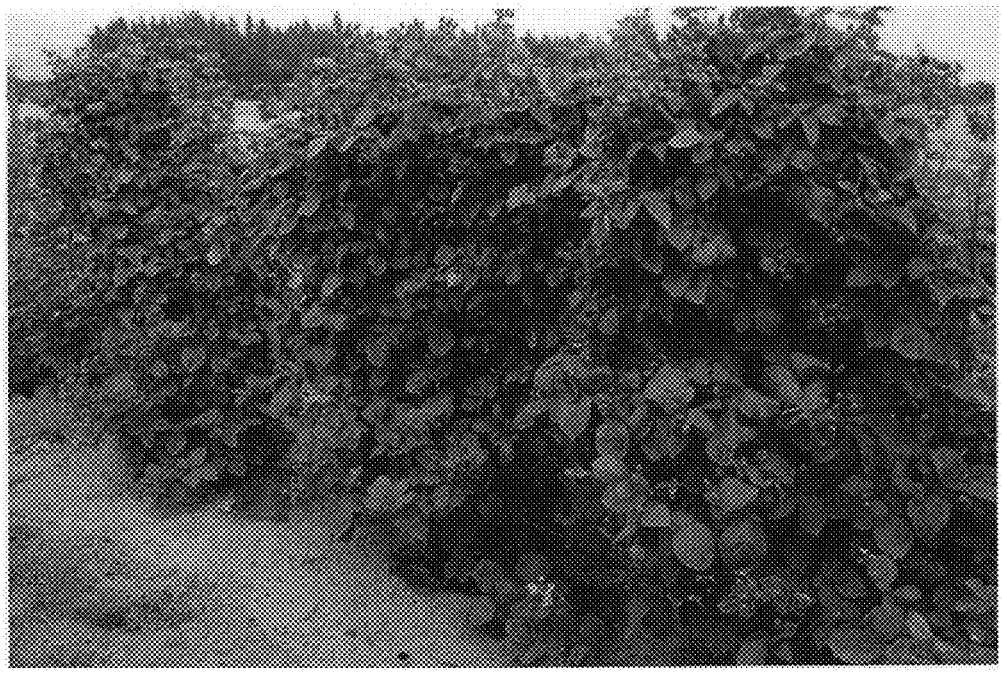

FIG. 4. shows an entire flowering 4-year old 'Galaxy' plant. As is typical for commercial production, semi-erect blackberry primocanes are topped at ~1 m and the primocanes and laterals that develop after topping are tied to a two wire trellis with the lower wire approximately 1.0 m above the ground and the upper wire approximately 1.5 m above the ground.

DETAILED DESCRIPTION OF THE NEW CULTIVAR

The following description of 'Galaxy' is based on observations taken from 2007 to 2017 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic and cultural conditions. 'Galaxy' has not been observed under all possible environmental conditions. Color terminology follows The Royal Horticultural Society Colour Chart. London (R.H.S.) ($5^{th}$ edition, 2007).

Table 1 shows important plant characteristics of the new cultivar. Characteristics include plant vigor, growth habit, date 50% of fruit were ripe, weight of primary fruit, firmness of fruit flavor of fruit and winter tolerance in Aurora, Oreg. (45° 16' 49" N/122° 44' 50" W) and Lynden, Wash. (48° 56' 48" N/122° 27' 2" W).

TABLE 1

| Characteristic | 'Galaxy' |
|---|---|
| Plant vigor | High vigor, greater than 'Loch Ness' and 'Navaho', similar to 'Triple Crown' and less than 'Chester Thornless' |
| Growth habit | Semi-erect |
| Date 50% of fruit were ripe | 5 August, early compared to 'Triple Crown' and 'Chester Thornless' |
| Weight of primary fruit (g) | 8.27 g, Larger than 'Chester Thornless' and smaller than 'Triple Crown' |
| Firmness of fruit | Excellent, firmer than 'Triple Crown' and as firm as 'Chester Thornless' |
| Skin toughness of fruit | Excellent compared to 'Triple Crown' and similar to 'Chester Thornless' |
| Flavor of fruit | Very good compared to 'Chester Thornless', 'Loch Ness', or 'Navaho' |
| Winter tolerance in Aurora, Oregon (45 16' 49" N/ 122 44' 50" W) | Excellent (comparable to 'Triple Crown', 'Chester Thornless', and 'Navaho') |
| Winter tolerance in Lynden, Washington (48 56' 48" N/ 122 27' 2" W) | Excellent (comparable to 'Triple Crown', 'Chester Thornless', and 'Navaho') |

Table 2 shows floricane and mature primocane characteristics of the new cultivar. Characteristics include diameter at base, diameter at midpoint, diameter at terminus, internode length at base, internode length at midpoint, internode length at terminus, presence of spines further than 0.6 m from the soil surface, presence of spines less than 0.6 m from the soil surface, floricane color at base, floricane color at midpoint, floricane color at terminus, floricane lateral length, floricane lateral strength, primocane color at base, primocane color at midpoint, primocane color at terminus, floricane length, and floricane length (range).

TABLE 2

| Characteristic | 'Galaxy' |
|---|---|
| Diameter at base (cm) | 1.69 |
| Diameter at midpoint (cm) | 1.17 |

TABLE 2-continued

| Characteristic | 'Galaxy' |
|---|---|
| Diameter at terminus (cm) | 0.20 |
| Internode length at base (cm) | 4.83 |
| Internode length at midpoint (cm) | 3.49 |
| Internode length at terminus (cm) | 3.49 |
| Presence of spines further than 0.6 m from the soil surface | Absent |
| Presence of spines less than 0.6 m from the soil surface | Absent |
| Floricane color at base | 146A |
| Floricane color at midpoint | 146A |
| Floricane color at terminus | 146C |
| Floricane lateral length | Medium-long |
| Floricane lateral strength | Medium strong |
| Primocane color at base | 144B |
| Primocane color at midpoint | 144A blushed with 183A |
| Primocane color at terminus | 144A blushed with 178A |
| Floricane length (m) | 2.80 |
| Floricane length (range) (m) | 2.18-3.16 |

Table 3 shows primocane foliage characteristics of the new cultivar. Primocane characteristics include mature compound leaf width, mature compound leaf length, number of leaflets per primocane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, spine presence on leaves, pubescence on primocane leaflet: upper surface, pubescence on primocane leaflet: undersurface, primocane leaf color abaxial, primocane leaf color adaxial, petiole length, petiole color: upper surface, petiole color: undersurface, petiolule length: terminal leaflet, petiolule length: first distal leaflet, petiolule color: abaxial, petiolule color: adaxial, stipule length, stipule width, and stipule attitude.

TABLE 3

| Characteristic | 'Galaxy' |
|---|---|
| Mature compound leaf width (cm) | 21.10 |
| Mature compound leaf length (cm) | 12.53 |
| Number of leaflets per primocane compound leaf | 5.00 |
| Mature leaflet shape | Obtuse |
| Mature leaflet apex | Broadly acuminate |
| Mature leaflet base | Rounded/cordate |
| Mature terminal leaflet width (cm) | 8.52 |
| Mature terminal leaflet length (cm) | 8.75 |
| Mature first lateral leaflet width (cm) | 7.17 |
| Mature first lateral leaflet length (cm) | 8.60 |
| Leaflet margin | Doubly serrate |
| Leaflet serration teeth length | 0.15 |
| Leaflet serration teeth width at base | 0.26 |
| Spine presence on leaves | No |
| Pubescence on primocane leaflet: upper surface | Yes, light |
| Pubescence on primocane leaflet: undersurface | Yes, medium |
| Primocane leaf color abaxial | N137A |
| Primocane leaf color adaxial | 138B |
| Petiole length (cm) | 7.57 |
| Petiole color: upper surface | 144A streaked with 183C |
| Petiole color: undersurface | 144C |
| Petiolule length: terminal leaflet (cm) | 3.65 |
| Petiolule length: first distal leaflet (cm) | 1.80 |
| Petiolule color: abaxial | 144A streaked with 184A |
| Petiolule color: adaxial | N144C |

TABLE 3-continued

| Characteristic | 'Galaxy' |
|---|---|
| Stipule length (cm) | 1.16 |
| Stipule width (cm) | 0.06 |
| Stipule attitude | Curled |

Table 4 shows floricane foliage characteristics of the new cultivar. Floricane characteristics include mature compound leaf width, mature compound leaf length, number of leaflets per floricane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, pubescence on floricane leaflet: upper surface, pubescence on floricane leaflet: undersurface, floricane leaf color abaxial, floricane leaf color adaxial, petiole length, petiolule length: terminal leaflet, petiolule length: first distal leaflet, petiolule color: abaxial, petiolule color: adaxial, stipule length, and stipule width.

TABLE 4

| Characteristic | 'Galaxy' |
|---|---|
| Mature compound leaf width (cm) | 14.40 |
| Mature compound leaf length (cm) | 9.58 |
| Number of leaflets per floricane compound leaf | 2-5, typically 3 |
| Mature leaflet shape | Oval |
| Mature leaflet apex | Broadly acute |
| Mature leaflet base | Acute |
| Mature terminal leaflet width (cm) | 6.12 |
| Mature terminal leaflet length (cm) | 7.82 |
| Mature first lateral leaflet width (cm) | 4.93 |
| Mature first lateral leaflet length (cm) | 7.28 |
| Leaflet margin | Doubly serrate |
| Leaflet serration teeth length | 0.21 |
| Leaflet serration teeth width at base | 0.25 |
| Pubescence on floricane leaflet: upper surface | Yes, medium density |
| Pubescence on floricane leaflet undersurface | Yes, heavy |
| Floricane leaf color abaxial | N137B |
| Floricane leaf color adaxial | 137C |
| Petiole length (cm) | 5.30 |
| Petiole color adaxial | 144B |
| Petiole color abaxial | 144C |
| Petiolule length terminal leaflet (cm) | 1.73 |
| Petiolule length first distal leaflet (cm) | 1.95 |
| Petiolule color abaxial | 144A |
| Petiolule color adaxial | 144B |
| Stipule length (cm) | 1.05 |
| Stipule width (cm) | 0.13 |

Table 5 shows flower and flowering characteristics of the new cultivar. Flower and flowering characteristics include date 1st bloom, date full bloom, date last bloom, petal color, the number flowers per cluster, the number of petals per flower, flower diameter, petal length, petal width, and the number of sepals per flower.

TABLE 5

| Characteristic | 'Galaxy' |
|---|---|
| Date 1st bloom | 23-May |
| Date full bloom | 30-May |
| Date last bloom | 7-Jun. |
| Petal color | NN155B |
| Number flowers per cluster | 6.25 |
| Number of petals per flower | 5.44 |
| Flower diameter (cm) | 2.55 |
| Petal length (cm) | 0.90 |

TABLE 5-continued

| Characteristic | 'Galaxy' |
|---|---|
| Petal width (cm) | 0.65 |
| Number of sepals per flower | 5 |
| Peduncle length (cm) | 8.17 |
| Rachis length (cm) | 8.50 |
| Peduncle color | 178A |
| Cyme type | Elongate simple cyme |

Table 6 shows fruit and fruiting characteristics of the new cultivar. Fruit and fruiting characteristics include date 5% of fruit were ripe, date 50% of fruit were ripe, date 95% of fruit were ripe, weight of primary fruit, weight of secondary fruit, diameter of primary fruit at equator, diameter of 2° fruit at equator, diameter of 1° fruit at poles: tip, diameter of 1° fruit at poles: base, diameter of 2° fruit at poles: tip, diameter of 2° fruit at poles: base, berry length 1° fruit, berry length 2° fruit, ratio of primary fruit length to width, shape description, uniformity of berry shape, color when full ripe, number of drupelets per fruit, individual seed weight, glossiness, firmness, flavor, texture of fruit when chewed, drupelet skin resistance to abrasion, ease of separation of fruit from pedicel, machine harvestability, resistance to heat damage of fruit, berries per inflorescence—mean, berries per inflorescence range, soluble solids (%; in Brix), pH, titratable acidity (% as citric acid), yield (actual kg·plt$^{-1}$), disease response, and red berry mite response.

TABLE 6

| Characteristic | 'Galaxy' |
|---|---|
| Date 5% of fruit were ripe | 22-Jul. |
| Date 50% of fruit were ripe | 5-Aug. |
| Date 95% of fruit were ripe | 28-Aug. |
| Weight of primary fruit (g) | 8.27 |
| Weight of secondary fruit (g) | 7.53 |
| Weight of tertiary fruit (g) | 7.85 |
| Diameter of primary fruit at equator (cm) | 2.04 |
| Diameter of 2 fruit at equator (cm) | 2.08 |
| Diameter of 3 fruit at equator (cm) | 2.05 |
| Diameter of 1 fruit at poles: tip (cm) | 1.07 |
| Diameter of 1 fruit at poles: base (cm) | 1.76 |
| Diameter of 2 fruit at poles: tip (cm) | 1.18 |
| Diameter of 2 fruit at poles: base (cm) | 1.75 |
| Diameter of 3 fruit at poles: tip (cm) | 1.20 |
| Diameter of 3 fruit at poles: base (cm) | 1.77 |
| Berry length primary fruit (cm) | 2.77 |
| Berry length 2 fruit (cm) | 2.93 |
| Berry length 3 fruit (cm) | 3.12 |
| Ratio of primary fruit length to width | 1.36 |
| Shape description | Uneven conical to barrel |
| Uniformity of berry shape | Good |
| Color when full ripe | 203B |
| Number of drupelets per fruit | 100.17 |
| Total seed weight per fruit (mg) | 323.73 |
| Individual seed weight (mg) | 3.23 |
| Glossiness | Medium gloss |
| Firmness | Very firm |
| Flavor | Very good |
| Texture of fruit when chewed | Good |
| Drupelet skin resistance to abrasion | Very good |
| Ease of separation of fruit from pedicel | Good |
| Machine harvestability | Good |
| Resistance to heat damage of fruit | Fair |
| Berries per inflorescence - mean | 6.40 |
| Berries per inflorescence range | 6-7 |
| Soluble solids (%; in Brix) | 12.76 |
| pH | 3.48 |
| Titratable acidity (% as citric acid) | 11.86 |
| Yield (actual kg·plt-1) | 7.71 |

TABLE 6-continued

| Characteristic | 'Galaxy' |
|---|---|
| Disease response | Under a typical, minimal, disease management program does not exhibit any particular disease problems |
| Red berry mite response | Susceptible but fewer symptoms than on 'Triple Crown' |

COMPARISON WITH PARENTAL AND COMMERCIAL CULTIVARS

'Galaxy' differs from the female parent blackberry plant 'ORUS 1393-1' (unpatented) in that 'Galaxy' is thornless and the fruit have a sweet, pleasant flavor and are more uniformly shaped, while 'ORUS 1393-1' has thorny canes and the fruit are slightly bitter and the drupelets are unevenly set.

'Galaxy' differs from the male parent blackberry plant 'Triple Crown' (unpatented) in that it is earlier ripening (50% ripe fruit on 5 August) with medium sized (6.52 g) fruit that are firm with a tough skin, while 'Triple Crown' (unpatented) is mid-season ripening (16 August) with large (7.50 g) fruit that are soft with tender skin.

'Galaxy' is earlier ripening than other commercial semi-erect blackberries such as 'Triple Crown' (unpatented), 'Navaho' (U.S. Plant Pat. No. 6,679), or 'Chester Thornless' (unpatented). 'Galaxy' ripens 4-5 d later than the semi-erect blackberry 'Loch Ness' (U.S. Plant Pat. No. 6,782) but is more vigorous growing and has firmer fruit with better flavor. 'Galaxy' is not typically as high yielding as 'Chester Thornless' (unpatented) or 'Triple Crown' (unpatented). The fruit of 'Galaxy' are firm and have a tough skin like those of 'Chester Thornless' (unpatented) and are firmer and much tougher skinned than 'Triple Crown' (unpatented) fruit. 'Galaxy' fruit are sweeter than those of 'Chester Thornless' (unpatented) but not as sweet as those of 'Navaho' (U.S. Plant Pat. No. 6,679) or 'Triple Crown' (unpatented).

'Galaxy' is primarily suited to fresh market sales, although it can be machine-harvested for the processed fruit market. 'Galaxy' fruit have been stored for 14 days in a plastic clamshell at 0 C with no mold and while retaining its firmness and skin resistance to abrasion.

We claim:

1. A new and distinct cultivar of thornless blackberry plant, substantially as illustrated and described, characterized by its medium-large sized fruit that are sweet, firm and have a tough skin and that ripen earlier than most semi-erect blackberry cultivars.

* * * * *